US00PP08710P

United States Patent [19]

Bartels et al.

[11] Patent Number: Plant 8,710

[45] Date of Patent: May 3, 1994

[54] SOLIDAGO PLANT NAMED YELLOW SUBMARINE

[75] Inventors: G. B. H. Bartels, Hornweg 53, 1432, GD Aalsmeer; Cees van Diepen, Venhuizen, both of Netherlands

[73] Assignee: G. B. H. Bartels, Aalsmeer, Netherlands

[21] Appl. No.: 86,145

[22] Filed: Jul. 6, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—G. B. H. Bartels

[57] ABSTRACT

A distinct cultivar of solidago plant named Yellow Submarine, characterized by its open and spreading flower form, abundance of flowering stems, long flowering stems, early flowering, high and low temperature stress resistance and good postharvest keeping quality.

1 Drawing Sheet

The present invention relates to a new and distinctive cultivar of Solidago hybrid hereinafter referred to by the cultivar name Yellow Submarine.

The new cultivar was developed by us at Bartelstek, Aalsmeer, Holland, through controlled breeding by crossing *Solidaster luteus* 'Lemore' as the female parent with the solidago cultivar identified as 86-32-06 as the male parent.

Asexual reproduction of the new cultivar by terminal or stem cuttings taken at Aalsmeer, Holland, has shown that the unique features of this new aster are stabilized and are reproduced true to type in successive generations of asexual reproduction.

The following characteristics distinguish the new solidago from both its parent varieties and other cultivated solidagos of this type known and used in the floriculture industry:

1. Yellow Submarine has a more open flower form that is more spreading than upright.
2. Yellow Submarine has an abundance of flowering stems.
3. Yellow Submarine has long flowering stems making it suitable as a cut flower.
4. Flowering is earlier on plants of Yellow Submarine.
5. Yellow Submarine is high and low temperature stress-resistant.
6. Cut flowering stems of Yellow Submarine consistently demonstrate good postharvest keeping quality.

The accompanying colored photograph illustrates the overall appearance and flower color of the new cultivar, showing the colors as true as it is reasonable possible to obtain in colored reproductions of this type. The photograph is a single flowering stem of Yellow Submarine.

The new cultivar can be compared in certain characteristics to the female parent *Solidaster luteus* 'Lemore'. In general comparison to *Solidaster luteus* 'Lemore', Yellow Submarine has:

1. A more open flower form than *Solidaster luteus* 'Lemore'.
2. More flowering stems, Yellow Submarine plants product 30 percent more stems per plant than plants of *Solidaster luteus* 'Lemore'.

3. Longer flowering stem, Yellow Submarine flowering stems are 20 cm taller than *Solidaster luteus* 'Lemore'.
4. More high and low temperature tolerance than *Solidaster letus* 'Lemore'.
5. An inflorescence arrangement that is more spreading than upright like *Solidaster luteus* 'Lemore'.
6. Cut flowering stems with postharvest keeping quality that is 7 to 8 days longer than *Solidaster luteus* 'Lemore'.

The following is a detailed description of our new cultivar based on plants produced under normal commercial practica in Aalsmeer, Holland, in a glass-covered greenhouse with day temperatures of 20° C. and night temperatures of 12° C. during the vegetative phase and day temperatures of 22° to 25° C. and night temperatures of 18° C. during the flowering phase.

Color references are made to The Royal Horticultural Society Colour Chart except where general terms of ordinary dictionary significance are used.

Botanical classification: Solidago hybrid cv Yellow Submarine.

Parentage:

*Male parent.*—86-23-06 solidago.

*Female parent.*—*Solidaster luteus* 'Lemore'.

Propagation:

A. *Type.*—By terminal tip cuttings, tissue culture and division.

B. *Time to initiate roots.*—21 days at 25° C. during the summer.

C. *Time to initiate roots.*—26 days at 20° C. during the winter.

D. *Rooting habit.*—Fibrous, branching.

Plant description:

A. *General appearance.*—Spreading, freely branching and vigorous.

B. *Foliage description.*—Shape: narrow, elliptic, tip acute. Size: 15 cm in length, 2.2 cm in width. Texture: Fine pubescence on leaf top side. Margin: Serrated at tip, 10 to 20 large teeth at leaf tip. Color: Young foliage top side: 147A. Young foliage under side: 147B. Mature foliage top side: 147A. Mature foliage under side: 147B. Venation: Parallel, branched, color is 147A.

Flowering description:

A. *Flowering habit.*—Panicles of florets, globose, loose arrangement, radiate capitula.

B. *Natural flowering season.*—Natural flowering season is the fall in the northern hemisphere.

C. *Quantity of inflorescences.*—16 to 20 lateral stems per terminal with 120 to 150 inflorescences per lateral stem.

D. *Ray florets.*—Shape: Ligulate. Color: Top side: 9C. When opening: 9B. Fading to: 9D. Under side: 9C. Number of ray florets: More than 15 per inflorescence. Size of inflorescence: 0.8 cm in diameter.

E. *Disc florets.*—Shape: Tubular. Color: Color mature: 9A. Color immature: 9B. Number of disc florets: More than 10 per inflorescence. Diameter of disc: 0.3 cm.

F. *Reproductive organs.*—Stamens: Anther color: 9B. Pollen color: 9B. Pistils: Stigma color: 9D. Style color: 144C.

Disease resistance: No fungal or bacterial problems observed to date.

I claim:

1. A new and distinct cultivar of solidago plant named Yellow Submarine, as illustrated and described.

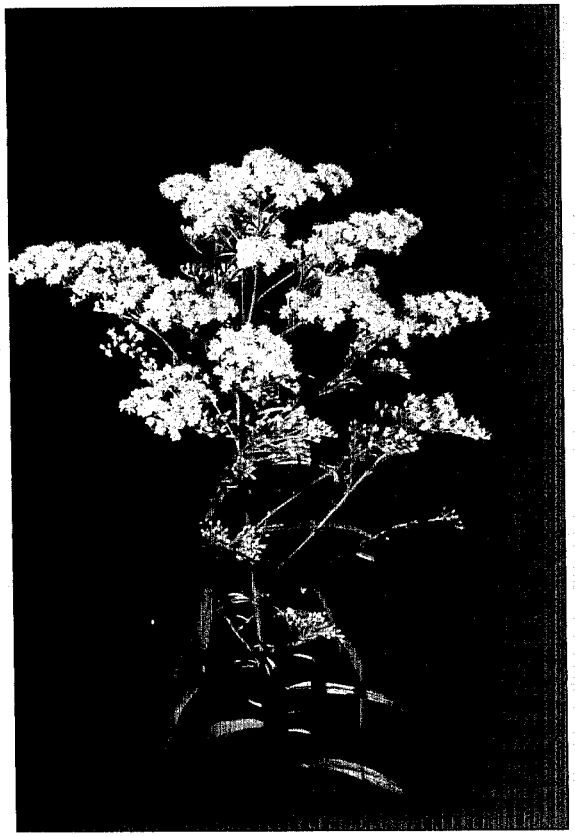

* * * * *